US012725206B1

(12) United States Patent
Smith

(10) Patent No.: US 12,725,206 B1
(45) Date of Patent: Sep. 1, 2026

(54) METHOD OF ASSESSING AN EXPECTED AGGREGATE ACCIDENT SEVERITY FOR A PLURALITY OF PERSONS DURING A STANDARD TIME PERIOD

(71) Applicant: Applied Underwriters, Inc., Omaha, NE (US)

(72) Inventor: Justin N. Smith, Belmont, CA (US)

(73) Assignee: Applied Underwriters, Inc., Omaha, NE (US)

( * ) Notice: Subject to any disclaimer, the term of this patent is extended or adjusted under 35 U.S.C. 154(b) by 74 days.

(21) Appl. No.: 16/798,503

(22) Filed: Feb. 24, 2020

Related U.S. Application Data

(60) Provisional application No. 62/811,596, filed on Feb. 28, 2019.

(51) Int. Cl.

| | |
|---|---|
| ***G06Q 40/08*** | (2012.01) |
| ***G06F 3/01*** | (2006.01) |
| ***G16H 40/67*** | (2018.01) |
| ***G16H 50/30*** | (2018.01) |

(52) U.S. Cl.
CPC ............. *G06Q 40/08* (2013.01); *G06F 3/015* (2013.01); *G06F 3/017* (2013.01); *G16H 40/67* (2018.01); *G16H 50/30* (2018.01); *G06F 2203/011* (2013.01)

(58) Field of Classification Search
CPC ........ G06Q 40/08; G16H 50/30; G16H 40/67; G06F 3/017; G06F 3/015; G06F 2203/011
USPC ........................................................ 705/4, 35
See application file for complete search history.

(56) References Cited

U.S. PATENT DOCUMENTS

| | | | | |
|---|---|---|---|---|
| 6,579,233 | B2 | 6/2003 | Hursh | |
| 7,384,394 | B2 | 6/2008 | Hursh et al. | |
| 7,908,157 | B1 | 3/2011 | Menzies et al. | |
| 8,075,484 | B2 * | 12/2011 | Moore-Ede ............ | B60K 28/06 128/920 |
| 9,747,722 | B2 | 8/2017 | Adler et al. | |
| D800,596 | S | 10/2017 | Ling et al. | |
| 2006/0200008 | A1 * | 9/2006 | Moore-Ede ............ | B60K 28/06 128/920 |
| 2008/0161654 | A1 * | 7/2008 | Teller ..................... | A61B 5/369 600/300 |
| 2014/0081179 | A1 * | 3/2014 | Moore-Ede ............ | G16H 50/30 600/595 |
| 2015/0182113 | A1 | 7/2015 | Utter, II | |

(Continued)

OTHER PUBLICATIONS

Occupational Fatigue Prediction for Entry-Level Construction Workers in Material Handling Activities Using Wearable Sensors Wonil Lee (Year: 2018).*

(Continued)

*Primary Examiner* — William E Rankins
(74) *Attorney, Agent, or Firm* — Marin Patents LLC; Gustavo Marin

(57) ABSTRACT

An expected aggregate accident severity for a group of people during a standard time period can be determined by asking each one of the people to wear a health tracker on their wrist during an evaluation period. The health tracker can monitor their sleep patterns and forecast an expected fatigue level when they work. The fatigue levels will correlate to the expected frequency of work-related accidents. The expected severity of the accidents will be related to the types of occupations each person has.

2 Claims, 2 Drawing Sheets

(56) References Cited

U.S. PATENT DOCUMENTS

2021/0113099 A1* 4/2021 Rogers ................ A61B 5/4803

OTHER PUBLICATIONS

KWIC PreviewUnconstrained smartphone sensing and empirical study for sleep monitoring and self-management Huang, Ke (Year: 2015).*
Czeisler (Year: 1978).*
WebPT, 3 Emerging Trends in OT Telehealth and Technology, https://www.webpt.com/blog/post/3-emerging-trends-in-ot-telehealth-and-technology/, last viewed Feb. 12, 2020.
Wayne Rosenkrans, Flight Safety Foundation | AeroSafetyWorld |HumanFactors; Too Tired; Wake, sleep and alertness measurements reveal a serious underestimation of cabin crew fatigue dated Dec. 2010-Jan. 2011, last viewed Feb. 14, 2020.
Bettger et al., The Authors, Published By The Journal of Bone and Joint Surgery, Incorporated; Effects of Virtual Exercise Rehabilitation In-Home Therapy Compared with Traditional Care After Total Knee Arthroplasty; VERITAS, a Randomized Controlled Trial; last viewed Feb. 12, 2020.
Bowen et al., Evaluating Low-cost Activity Trackers for Use in Large-scale Data Gathering of Forestry Workers, last viewed Feb. 14, 2020.
CATERPILLAR®, Caterpillar Safety Services, Reducing Fatigue Risk; Optimize Tehnology and Culture to See, Mitigate and Manage an Invisible Threat, last viewed Feb. 13, 2020.
CAT® Smartband, Caterpillar Safety Services, Managing Fatigue, See Risk Coming with Predictive Fatigue Monitoring, last viewed Feb. 13, 2020.
Sarah De Crescenzo; Xconomy, Study: Reflexion Health Virtual Therapy System reduces Rehab Costs dated Oct. 15, 2018, https://xconomy.com/san-diego/2018/10/15/study-reflextion-health-virtual-therapy-system-reduces-rehab-costs/, last viewed Feb. 12, 2020.
Fatigue Science: Predictive fatigue management for industry and elite sport; Choose Your Path to Readi; https://www.fatiguescience.com/readiband/, last viewed Feb. 17, 2020.
Peter G. Roma et al., Federal Aviation Administration, Flight Attendance Fatigue Recommendation II: Flight Attendant Work/Rest Patterns, Alertness, and Performance Assessment dated Dec. 2010, last viewed Feb. 14, 2020.
Dr. Joseph Louis et al., Improving Safety in Work Zones by Using Real-Time Tracking of Worker Field of View and Proximity to Hazards, Final Project Report, last viewed Feb. 13, 2020.
Fitbit, Help article: What's sleep score in the Fitbit app?, last viewed Feb. 13, 2020.
Tom Jackson, How Caterpillar's Fitbit-like Smartband can just about predict when a heavy equipment accident will happen dated Oct. 3, 2016, https://www.equipmentworld.com/how-caterpillars-fitbit-like-smartband-can-just-about-predict-when-a-heavy-equipment-accident-will-happen/, last viewed Feb. 13, 2020.
Kevin Huang, Exploring In-Home Monitoring of Rehabilitation and Creating an Authoring Tool for Physical Therapists dated Dec. 2015, last viewed Feb. 12, 2020.
Kevin Huang et al., A Technology Probe of Wearable In-Home Computer-Assisted Physical Therapy, Session: Interactive Technologies for Rehabilitation, last viewed Feb. 12, 2020.
Hani A. Kayyali et al., Orginal Research, Remotely Attended Home Monitoring of Sleep Disorders, last viewed Feb. 14, 2020.
Medrisk, 2019 Indiustry Trends Report, Physical Medicine and Workers' Comp, MedRisk Publishes White Paper on Telerehabilitation in Workers' Compensation, https://www.medrisknet.com/news/medrisk-publishes-white-paper-telerehabilitation-workers-compensation/, last viewed Feb. 12, 2020.
Medrisk, Telerehabilitation & the Injured Worker: A Practical Guide, last viewed Feb. 12, 2020.
The Patient Safety Company®, Occupational Health Tracker, last viewed Feb. 12, 2020.
Canadian Sleep Institute, Development of a North-American Fatigue Management Program for Commercial Motor Carriers Phase II (Pilot Study) dated Jan. 2006, last viewed Feb. 14, 2020.
Gross & Kenny, LLP; Philadelphia Workers' Compensation Lawyers: New Smartband Technology dated Nov. 30, 2016, https://www.philaworkerscomp.com/2016/11/30/philadelphia-workers-compensation-lawyers-smartband-technology/, last viewed Feb. 13, 2020.
Fatigue Science, The Science of Sleep and Workplace Fatigue e-book, last viewed Feb. 14, 2020.
Clear Employer Services, Sleep Deprivation Can Impact Your Workers Company, https://www.clearemployerservices.com/sleep-deprivation-can-impact-your-workers-comp/, last viewed Feb. 12, 2020.
Judy Bowen et al., Working Paper Series ISSN 1177-777X, Investigating the Use of Activity Trackers to Observe High-Risk Work Environments, Working Paper: Jan. 2015 Nov. 2015, last viewed Feb. 14, 2020.
U.S. Department of Transportation, Federal Railroad Administration, Validation and Calibration of a Fatigue Assessment Tool for Railroad Work Schedules, Summary Report Oct. 2006, last viewed Feb. 14, 2020.

* cited by examiner

METHOD OF ASSESSING AN EXPECTED AGGREGATE ACCIDENT SEVERITY FOR A PLURALITY OF PERSONS DURING A STANDARD TIME PERIOD

COPYRIGHT AND TRADEMARK NOTICE

A portion of the disclosure of this patent document contains material to which a claim for copyright is made. The copyright owner has no objection to the facsimile reproduction by anyone of the patent document or the patent disclosure, as it appears in the Patent and Trademark Office patent file or records but reserves all other copyright rights whatsoever.

BACKGROUND OF THE INVENTION

Field of the Art

Embodiments of the present invention relate to wearable health trackers for underwriting.

Discussion of the State of the Art

Workers' Compensation (WC) is a government-run system which controls the liability of employers for work-related injuries to their employees.

Every U.S. state has its own WC system.

Most employers are required to buy WC insurance coverage.

WC claimants are individual employees, but the client is the employer.

Total U.S. WC insurance premium revenue exceeds $50 billion per year.

In most states, and for most insurers, the computed premium for WC insurance coverage is based on total payroll paid by the employer during the coverage term.

The employer usually reports aggregate payroll by occupation to the insurer.

Each occupation has an associated expected work-related accident severity per unit payroll.

The payroll times the expected work-related accident severity per unit payroll is a quantitative measure of the expected aggregate accident severity for a covered employee.

Accident severity may be quantified by the dollar value of the medical care and lost income of a person suffering a work-related injury. A WC claim is a useful way to measure accident severity. Expected accident severity is a measure of expected WC claims for a future standard time period.

The insurer usually never discovers much about individual employees (like: experience level, fitness level, where they work, whether they are full or part-time, or even how many employees there are) unless they file a claim for a work-related injury they have suffered.

The insurer usually has some freedom to vary the premium charged to an employer based on that employer's individual risk characteristics. Any information about their employees could be useful in this process. The premium for the employer must be large enough to cover the expected aggregate accident severity for the employees of the company during a standard time period. A standard time period for WC coverage is about a year. Other standard time periods may be suitable, such as a fraction of a year or multiple years. "Employees of a company" is an example of a plurality of persons. As used herein, a "plurality of persons" contemplates a single person, such as an employer with a single employee.

There is a need, therefore, for a computer-implemented method of assessing an expected aggregate accident severity for a plurality of persons during a standard time period based on measured characteristics of each of the persons in said plurality of persons.

SUMMARY OF THE INVENTION

The summary of the invention is provided as a guide to understanding the invention. It does not necessarily describe the most generic embodiment of the invention or the broadest range of alternative embodiments.

A health-tracking event used for WC underwriting could comprise:

A contest run between an employer's employees over a short but significant evaluation period, long enough to generate a material amount of data on health-related characteristics of the employees. As used herein, a short but significant evaluation period may be in the range of one day to one month. Longer and shorter evaluation periods may be suitable depending upon the application.

BRIEF DESCRIPTION OF THE DRAWING FIGURES

DETAILED DESCRIPTION

Figure 1:
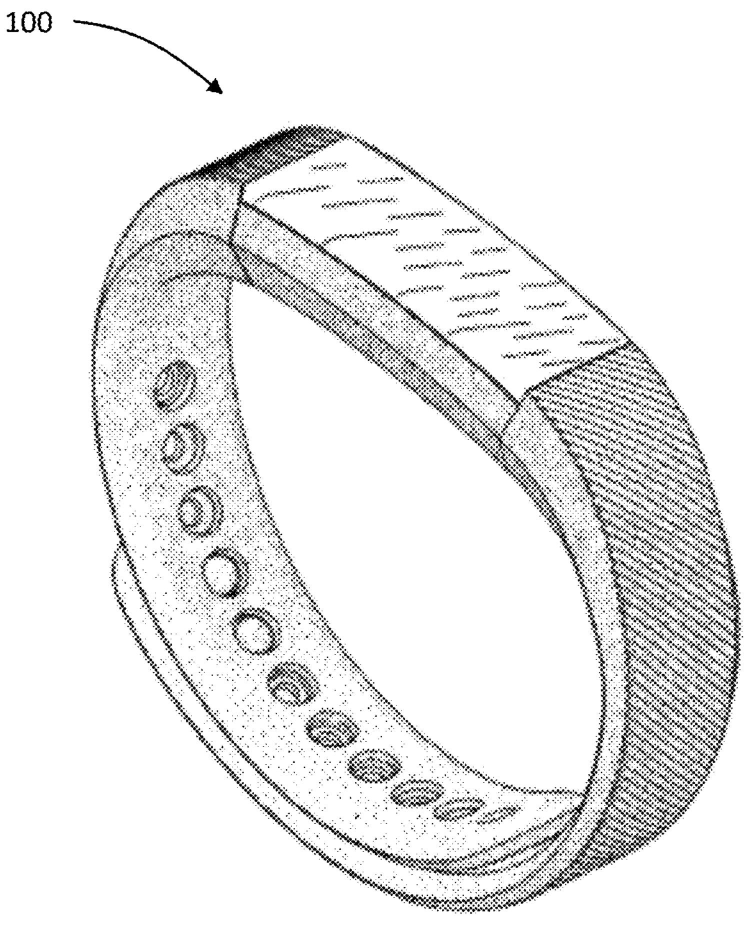
FIG. 1 is a perspective drawing of a prior art wrist wearable health tracker.

The detailed description describes non-limiting exemplary embodiments. Any individual features may be combined with other features as required by different applications for at least the benefits described herein. As used herein, the term "about" means plus or minus 10% of a given value unless specifically indicated otherwise.

As used herein, a "computer-based system" comprises an input device for receiving data, an output device for outputting data in tangible form (e.g. printing or displaying on a computer screen), a permanent memory for storing data as well as computer code, and a microprocessor for executing computer code wherein said computer code resident in said permanent memory will physically cause said microprocessor to read-in data via said input device, process said data within said microprocessor and output said processed data via said output device.

As used herein, a device that is configured to carry out a method step contemplates that the device comprises a computer-based system with appropriate computer code to execute the method steps.

As used herein, a "server" is a computer-based system in digital or analog communication with a peripheral device, said server being programed to execute method steps based on input from the peripheral device. As described in more detail below, the sensors in a wrist wearable health-tracking device are examples of peripheral devices. A server relative to the sensors may include one or more of a CPU physically located within said wrist wearable health-tracking device and digital or analog communication with said sensors, a phone in digital communication with said wrist wearable health-tracking device, and a cloud-based instance in digital communication with said phone. As used herein, a "cloud-based instance" can be any computer-implemented device in digital communication with said phone. A cloud-based instance may be provided by a cloud service provider, such as Amazon EC2, or a private instance, such as a person's desktop computer.

As used herein, the term "shaped" means that an item has the overall appearance of a given shape even if there are minor variations from the pure form of said given shape.

As used herein, the term "generally" when referring to a shape means that an ordinary observer will perceive that an object has said shape even if there are minor variations from said shape.

As used herein, relative orientation terms, such as "up", "down", "top", "bottom", "left", "right", "vertical", "horizontal", "distal" and "proximal" are defined with respect to an initial presentation of an object and will continue to refer to the same portion of an object even if the object is subsequently presented with an alternative orientation, unless otherwise noted.

A health-tracking event used for WC underwriting could comprise:

A contest run between an employer's employees over a short but significant period of time, long enough to generate a material amount of data on health-related characteristics of the employees. One day to one month is suitable.

Any other event organized by an employer or a third party for said employees.

The event could be structured with:

A device worn by each employee that tracks their activity level over time, perhaps including any or all of: steps taken (how many and perhaps also when), time spent sleeping (duration, begin and end times, and quality), blood oxygen levels, heart rate, and other indicators of physical activity and stress. The devices may also track location using GPS technology. A suitable device is a wrist wearable health-tracking device. A wrist wearable health-tracking device will be described in more detail below with respect to FIG. 1.

A smartphone application (app) to synchronize data from the wearable devices and transmit it to a central server, and to relay ongoing contest information (such as progress towards goals, leaderboards) to the employees.

Suitable wrist wearable health-tracking devices include the CAT® SmartBand. The CAT® SmartBand is a wrist worn device that measures a worker's sleep patterns. Readi™ software by Fatigue Science correlates sleep patterns with subsequent worker fatigue levels. High fatigue levels lead to more accidents. Hence data from a CAT® SmartBand would be useful in workers' compensation underwriting. Readi™ software has also been ported to Fitbit® devices and Garmin™ devices.

A suitable method for evaluating task effectiveness based on sleep patterns is described in U.S. Pat. No. 6,579,233 B2 "System and Method for Evaluating Task Effectiveness Based on Sleep Pattern" (Hursh). Said patent is incorporated herein by reference with specific reference to the impact of circadian rhythms on performance (e.g. FIG. 2).

The effectiveness output of the model is determined by three major factors: the endogenous circadian rhythm of performance and arousal, the current balance in the sleep reservoir, and the sleep inertia, a temporary debilitating influence during the period immediately following awakening. The magnitude of sleep inertia is a function of sleep intensity at time of awakening and generally dissipates within two hours. Because these factors work together to determine the net rate of change in performance, the model must keep track of the sleep reservoir balance moment by moment over time. This requires integration or accumulation of gains and losses of sleep reservoir units during each minute of the schedule.

Performance is modulated by the circadian rhythm, a sinusoidal pattern with a period of approximately 24 hours that is in general synchronized with the normal day-night cycle. The circadian oscillator provides continual real-time output that can be used to determine modulation of performance. The circadian process C produces two simultaneous but independent outputs: (1) modulation of performance through changes in arousal, and (2) modulation of sleep propensity SP, the ability to fall asleep and maintain sleep. The two circadian outputs are approximately 180 degrees out of phase. Peak arousal occurs during the evening at about 2000 hours and peak sleep propensity at about 0400 hours.

The circadian rhythm is composed of the sum of two underlying sinusoidal oscillators. The basic oscillator has a period of 24 hours and a secondary oscillator has a period of 12 hours. The two oscillators are out of phase, producing a wave form that more closely resembles the actual circadian pattern of arousal level, which is typically low in the early morning and has two peaks, one in the late morning and the other in the early evening.

The circadian rhythm is represented by a function, C:

$$C=\mathrm{COS}(2\Pi(t-p)/24)+\beta(\mathrm{COS}(4\Pi(t-p-p')/24))$$

where, t is clock hour (1-24), β is the relative amplitude of the 12-hour oscillator (0.5), p is the phase of the primary 24-hour oscillator (normally about 1700 hrs), and p' is the relative phase of the 12-hour oscillator relative to the primary oscillator (normally about −3 hours).

Sleep propensity has three components: the endogenous circadian rhythm of sleepiness C, a sleep debt S that accumulates during waking and decreases during sleep, and a constant m for the mean or midline value. Sleep propensity, SP, is represented by the equation:

$$SP=m-(a\cdot C)$$

where a is an amplitude constant (approximately 0.55). Sleep propensity is at its highest level in the early morning hours, reaching a peak at about 0400 hours and a minimum in the early evening at about 2000 hours. Sleep intensity SI is determined by the level of sleep propensity, modified by the current sleep debt in the sleep reservoir:

$$SI=SP+S$$

The sleep reservoir represents the current balance of the critical resources needed to maintain performance. It can be thought of as the current level of a rechargeable battery whose charge level is determined by sleep intensity and whose discharge rate is determined by waking activity. The reservoir has a maximum capacity of 2880 units. As activity builds up, resources in the reservoir are depleted and performance capability declines. The rate of loss during waking is assumed to be linear. While asleep, resources are replenished as a function of the sleep intensity. The level of the reservoir ranges from 0 to 2880 units (the equivalent of 2 days awake or approximately 4 days of restricted sleep). The rate of discharge during waking activity is 0.5 units per minute or 30 units per hour.

The effectiveness output of the model is determined by three major factors: the endogenous circadian rhythm of performance and arousal, the current balance in the sleep reservoir, and the sleep inertia, a temporary debilitating influence during the period immediately following awakening. The magnitude of sleep inertia is a function of sleep intensity at time of awakening and generally dissipates within two hours.

Because these factors work together to determine the net rate of change in performance, the model must keep track of the sleep reservoir balance moment by moment over time. This requires integration or accumulation of gains and losses of sleep reservoir units during each minute of the schedule. Performance is modulated by the circadian rhythm, a sinusoidal pattern with a period of approximately 24 hours that is in general synchronized with the normal day-night cycle.

FIG. 1 is a rendering of a prior art wrist wearable health-tracking device 100 for measuring a person's sleep patterns, hence subsequent fatigue levels, hence propensity to have a work-related accident during a subsequent work period. Said figure corresponds to FIG. 7 of U.S. design Pat. No. D800,596 S "Wearable Fitness Band" (Ling et al.). Said design patent is assigned to Fitbit, Inc., and is incorporated herein by reference.

A suitable wrist wearable health-tracking device may comprise an accelerometer and three axis-gyroscope. These provide suitable signals for determining wrist and arm motion, and hence sleep. The wrist wearable health-tracking device may also comprise a pulse monitor, temperature sensor and/or blood oxygen monitor. Signals from these sensors can help determine stages of sleep. A wrist wearable health-tracking device or phone carried by a user in digital communication with said wrist wearable health-tracking device may comprise a global positioning system (GPS). This can help monitor a worker's activities and movements during the day.

Registration of the employee via the app for the event could also include input of information about the employee, such as:

- A uniquely identifying code;
- Age;
- Gender;
- Job function, years of experience in this function, years with this employer, and current average weekly compensation; and
- Self-assessed fitness data, such as: weight, height, general activity level.

The use of an app may not be needed in all cases, but it would facilitate user registration.

Without an app, the employer would have to distribute devices and the insurer would have no guarantee that they were all distributed to employees, and no information about the particular employees, unless that information could be gathered by entering it into the device.

Any event-related information used to encourage participation (such as leaderboards) could be distributed to a website rather than to the app.

The event could proceed over the course of several days, to a week, to a month. The employees could be rewarded for their participation, perhaps with small prizes for the "winners" of various categories, though the prizes should not be large enough to encourage unusual or excessive activity levels. The data gathered and transmitted to the server could be made available to the insurer for underwriting purposes.

Certain data may not be usable, because underwriting on certain characteristics may be prohibited, even though individual employees would not suffer but only their employer. This may include age and gender.

Sleep habits would be directly useful to the insurer as there is data suggesting correlations between irregular sleep patterns and high accident rates among machinery operators.

High activity levels could indicate employees who are supposed to be in low-risk sedentary work actually perform more active, higher risk duties.

GPS data, if available, could be used to test information supplied by the employer to the insurer regarding the specific locations or radius of work locations.

The data transmitted to an insurer's server may be used as follows:

Any data which is gathered but which cannot be used (such as employee ages) would be immediately discarded.

Data from each individual employee may be combined by a formula or algorithm to produce one or more composite scores for each employee.

The scores for each employee would be combined in a weighted average employer score, where the individual scores are weighted by the average weekly compensation (potentially capped at the level that generates maximum WC indemnity benefits in the state of operation) multiplied by a premium rate applicable to the employee's declared job function in the state in which the employee works. The premium rate may comprise at least in part an expected work-related accident severity per unit payroll for an occupation of an employee.

The insurer could also make use of other data about the running of the event to formulate other employer scores, including:

What percentage of their employees (based on a stated employee count or on the number of wearable devices requested) register for the contest (employers who are able to drive activities such as these are generally more able to direct safe workplaces).

The employer scores calculated by the insurer may be used as follows:

If the employer is not yet a client for the insurer's insurance coverage, the scores could factor into the decision whether or not to sell insurance coverage to the employer, and at what rate.

If the employer is already a client, then if the employer agreed at the incept of the insurance policy period to have premium rates be subject to adjustment on completion of the event, the insurer could thus modify the employer's premium rates. Or the insurer could make a renewal/non-renewal decision based on the employer scores.

The event could be implemented for every employer that is an insurance client or potential client of the insurer, or employers could be targeted for inclusion based on their industry or actual loss performance.

The event could be implemented for every employer that is an insurance client or potential client of the insurer, or employers could be targeted for inclusion based on their industry or actual loss performance.

For example, employers in an industry (like trucking) where there is wide-scale use of machinery and shift patterns that may disrupt sleep patterns could be targeted for study of sleep data.

For another example, if an employer coming to the end of a policy period has been responsible for a relatively large number of losses, or of unusually large losses, it could be offered the chance to host an event which would allow the insurer to assess whether the result stemmed from sheer bad luck, or from characteristics of its workforce.

Events could be useful with all types and sizes of WC insurance clients. However, events would be most useful with insurance clients who do not take on any of the risk associated with coverage.

Clients with large-scale risk-sharing plans (including linear retrospectively rated premium plans, non-linear retrospectively rated premium plans, large deductible plans, and qualified self-insurance) take back a large part of the financial risk associated with their insurance coverage. Thus, insurers doing business with them have relatively lower levels of concern about the amount of insurance losses that is generated. Exemplary non-linear retrospectively rated premium plans are described in more detail in U.S. Pat. No. 7,908,157 B1 "Reinsurance Participation Plan", (Menzies et al.). Said patent is incorporated herein by reference with specific reference to the non-linear plans illustrated in FIGS. 5, 6, and 10—ISC.

Clients which pay "guaranteed cost" premiums pass all or substantially all of the risk associated with their losses to the insurer. Events are likely to be most useful with these clients.

Events could be useful for both large and small clients.

Premium rates and acceptability criteria for most types of insurance are highly regulated by state agencies, and state rules generally limit the kinds of information that an insurer can use and also the algorithms they can use.

It is unlikely that an insurer would be permitted to use information that directly affected the price or availability of coverage available to an individual person if that information was gained from an employer-organized contest, assuming that participation in the contest was encouraged by the employer.

It is thus unlikely that an insurer would be permitted to use event results to decide acceptability or rates for individual life insurance, annuities, individual accident or health insurance, or personal lines coverages such as auto insurance (even though sleep patterns probably would serve as a good rating variable for auto insurance).

However, it is likely that the information use could be permitted if it only affected availability or price of coverage to the employer (even if said coverage provides benefits to the employees) because the employer is responsible both for the selection of insurance coverage and the decision to participate in the contest.

As well as WC, the reasoning above suggests there may be applications to rating or acceptability decisions for: group health insurance (e.g. employer-sponsored and subsidized health and dental insurance plans); and group life, accident, or pension plans (e.g. employer-sponsored life insurance).

Note that voluntary group life and accident plans usually have low benefits and high premium rates because they must accept any members of the group wishing to buy coverage. Because there are likely to be some high-risk individuals working for every large employer, it is unlikely that contests would be useful in this setting, because regardless of healthiness of most workers, it is only the very least healthy who will purchase coverage.

Figure 2:
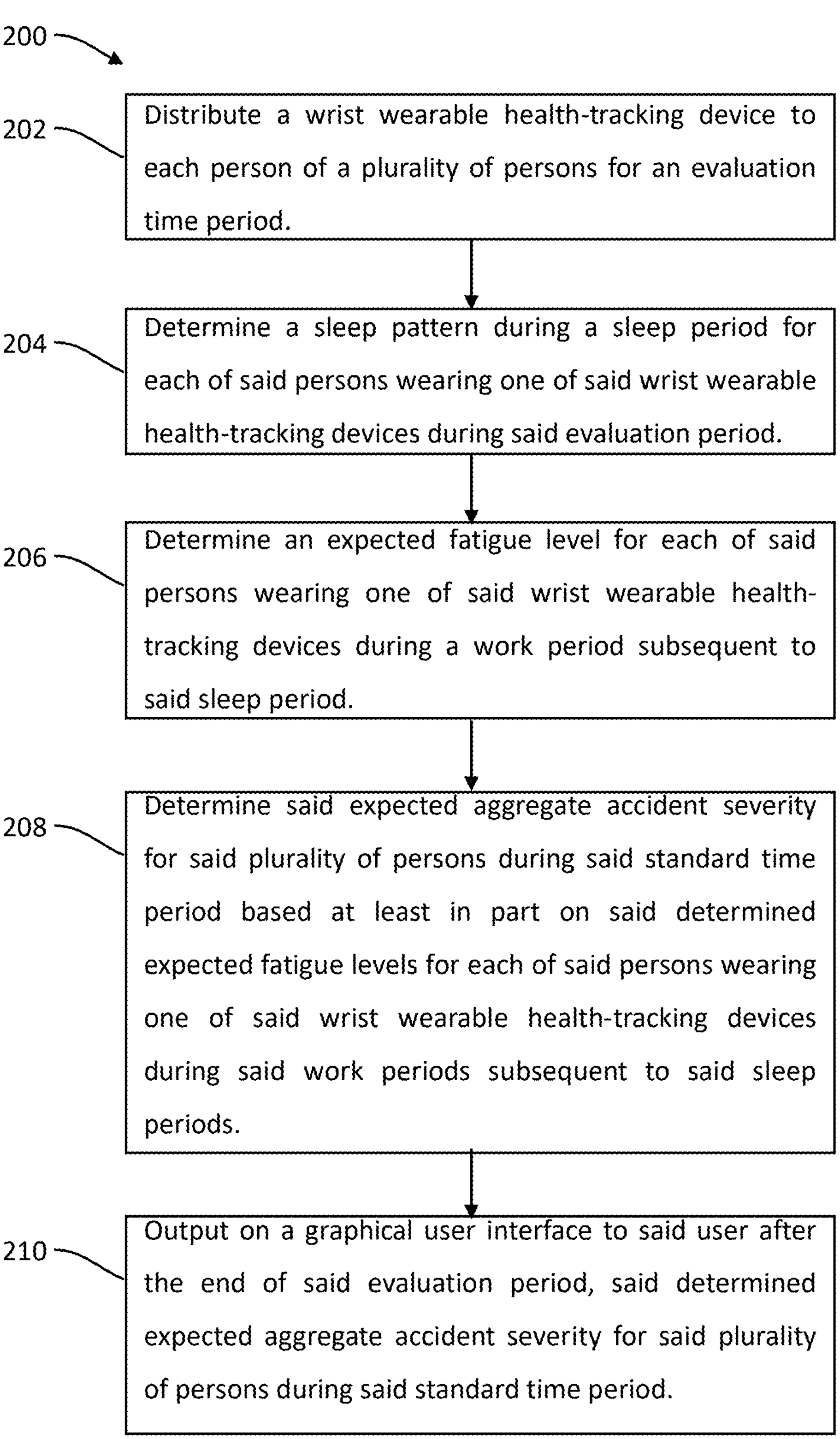
FIG. 2 is a flow chart of a computer-implemented method of assessing the expected aggregate accident severity for a plurality of persons during a standard time period

Method of Assessing an Expected Aggregate Accident Severity for a Plurality of Persons During a Standard Time Period FIG. 2 is a flow chart 200 of a computer-implemented method of assessing the expected aggregate accident severity for a plurality of persons during a standard time period.

The method may comprise the steps:

distribute 202 a wrist wearable health-tracking device (e.g. CAT® SmartBand) to each person (e.g. employee) of a plurality of persons (e.g. employees of an employer) for an evaluation time period (e.g. event or contest) wherein:

said wrist wearable health-tracking device comprises sensors including one or more of:

an accelerometer;

a three-axis gyroscope;

a body temperature sensor;

a pulse monitor; or a blood oxygen sensor said wrist wearable health-tracking device is in digital communication with a server (e.g. employee's smart phone, cloud-based instance, an/or insurer's server); and said server is configured to:

determine 204 a sleep pattern during a sleep period for a person wearing said wrist wearable health-tracking device (e.g. the method described in Hursh);

determine 206 an expected fatigue level for said person wearing said wrist wearable health-tracking device during a work period subsequent to said sleep period;

determine 208 said expected aggregate accident severity for said plurality of persons during said standard time period based at least in part on said determined expected fatigue levels for each of said persons wearing one of said wrist wearable health-tracking devices during said evaluation time period; and output 210 on a graphical user interface (e.g. computer screen) to a user (e.g. employer or insurer) after the end of said evaluation period, said expected aggregate accident severity for said plurality of persons during said standard time period;

determine by said server, a sleep pattern during a sleep period for each of said persons wearing one of said wrist wearable health-tracking devices during said evaluation period;

determine by said server, said expected fatigue level for each of said persons wearing one of said wrist wearable health-tracking devices during a work period subsequent to said sleep period;

determine by said server, said expected aggregate accident severity for said plurality of persons during said standard time period based at least in part on said determined expected fatigue levels for each of said persons wearing one of said wrist wearable health-tracking devices during said work periods subsequent to said sleep periods; and output on a graphical user interface to said user after the end of said evaluation period, said determined expected aggregate accident severity for said plurality of persons during said standard time period.

The sleep periods and work periods may all be during the evaluation period.

The server may be further configured to:

determine said expected aggregate accident severity for said plurality of persons during said standard time period based additionally at least in part on a payroll and an expected work-related accident severity per unit payroll for an occupation for each of said persons in said plurality of persons.

While the disclosure has been described with reference to one or more different exemplary embodiments, it will be understood by those skilled in the art that various changes may be made and equivalents may be substituted for elements thereof without departing from the scope of the disclosure. In addition, many modifications may be made to adapt to a particular situation without departing from the essential scope or teachings thereof. Therefore, it is intended that the disclosure not be limited to the particular embodiment disclosed as the best mode contemplated for carrying out this invention.

What is claimed is:

1. A computer-implemented method for computing and displaying an expected aggregate accident severity for a user over a time period, the method comprising the steps of:

synchronizing, at a network-connected server, a plurality of sensor readings from a network-connected wrist wearable health-tracking device associated with a user, the network-connected wrist wearable health-tracking device comprising:

an accelerometer and a three-axis gyroscope providing signals for determining wrist and arm motion to detect sleep; and a body temperature sensor, a pulse monitor, and a blood oxygen sensor providing signals to help determine stages of sleep;

modeling, by the server, circadian oscillators for the user based on the plurality of sensor readings, wherein the circadian oscillators comprise a first oscillator having a period of 24 hours and a second oscillator having a period of 12 hours, the first and second oscillators being out of phase to model variations in arousal level wherein the modeling implements the circadian oscillators by summing two cosine waves, the first cosine wave completing one cycle every 24 hours with phase centered at approximately 1700 hours, and the second cosine wave completing two cycles every 24 hours with half the amplitude and offset by approximately three hours earlier, the sum producing a composite waveform that represents the user's circadian rhythm based on the time of day extracted from the sensor readings;

determining, by the server, a sleep pattern of the user during a sleep period based on the plurality of sensor readings, wherein determining the sleep pattern comprises:

detecting sleep state transitions by analyzing changes in wrist and arm motion from the accelerometer and gyroscope signals, wherein reduced motion below a threshold indicates sleep onset and increased motion above a threshold indicates wake events;

tracking sleep quality by combining the motion data with physiological signals from the pulse monitor, temperature sensor, and blood oxygen sensor to identify sleep stages and disruptions;

generating the sleep pattern as a time-series record of sleep states, sleep stages, and fragmentation events over the sleep period;

calculating, by the server, an amount of effective sleep for the user based on the determined sleep pattern, wherein the effective sleep represents a cumulative measure of sleep recovery that increases during detected sleep periods and decreases during periods, the measure being adjusted based on sleep quality indicators from the sensor reading;

generating, by the server, a fatigue assessment for the user during a work period subsequent to the sleep period by combining the determined sleep pattern with the calculated amount of effective sleep and the current circadian phase, wherein the fatigue assessment indicates performance capability based on the physiological recovery tracked through the sensor readings;

generating, by the server, a real-time safety monitoring metric for the user based on correlation between the fatigue assessment and sleep pattern disruptions, wherein the metric quantifies deviations from baseline performance capability as measured through the continuous physiological monitoring;

automatically adjusting, by the server, safety protocols in response to the real-time fatigue assessment, including generating alerts when sensor-detected fatigue patterns indicate reduced performance capability below a safety threshold; and displaying, on a graphical user interface of the network-connected user device, the safety monitoring metric with visual alerts that change based on threshold comparisons of the real-time fatigue assessment;

repeating the synchronizing through displaying steps for each user in the plurality of users to generate aggregate safety monitoring metrics for the plurality of users during the time period based on the fatigue assessments of each user.

2. The method of claim 1 wherein the server comprises one or more of:

a user device; or a cloud-based instance.

* * * * *